(12) United States Patent
Doi et al.

(10) Patent No.: US 9,201,901 B2
(45) Date of Patent: Dec. 1, 2015

(54) TECHNIQUES FOR GENERATING A REPRESENTATIVE IMAGE AND RADIOGRAPHIC INTERPRETATION INFORMATION FOR A CASE

(71) Applicant: INTERNATIONAL BUSINESS MACHINES CORPORATION, Armonk, NY (US)

(72) Inventors: Munehiro Doi, Kanagawa (JP); Yumi Mori, Kanagawa-Ken (JP); Hiroki Nakano, Shiga (JP)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/365,337

(22) PCT Filed: Sep. 20, 2012

(86) PCT No.: PCT/JP2012/074077
§ 371 (c)(1),
(2) Date: Jun. 13, 2014

(87) PCT Pub. No.: WO2013/088807
PCT Pub. Date: Jun. 20, 2013

(65) Prior Publication Data
US 2014/0307938 A1    Oct. 16, 2014

(30) Foreign Application Priority Data

Dec. 13, 2011 (JP) ................................. 2011-272175

(51) Int. Cl.
*G06K 9/00* (2006.01)
*G06F 17/30* (2006.01)
(Continued)

(52) U.S. Cl.
CPC ........ *G06F 17/30253* (2013.01); *A61B 6/5235* (2013.01); *G06F 19/321* (2013.01); *G06F 19/3443* (2013.01); *G06K 9/4614* (2013.01); *G06K 2209/05* (2013.01)

(58) Field of Classification Search
CPC .................... G06F 17/30256; G06F 17/30253; G06F 17/30; G06F 19/321; G06F 19/3443; G06K 9/6215; G06K 2209/27
USPC .................................. 382/128, 191, 207, 305
See application file for complete search history.

(56) References Cited

U.S. PATENT DOCUMENTS 6,292,577 B1 * 9/2001 Takahashi ..................... 382/128
8,009,936 B2 * 8/2011 Oosawa et al. ............... 382/305
(Continued)

FOREIGN PATENT DOCUMENTS

| JP | 2002132831 A | 5/2002 |
| JP | 2004086538 A | 3/2004 |

(Continued)

OTHER PUBLICATIONS

International Application No. PCT/JP2012/074077, International Search Report.
(Continued)

*Primary Examiner* — John Strege
(74) *Attorney, Agent, or Firm* — Russell Ng PLLC; Matthew Baca

(57) ABSTRACT

A technique for generating a representative image representing a case and radiographic interpretation information for each case includes calculating wavelet features of a plurality of images that have been taken and stored in the past. The calculated wavelet features and extracted keywords are stored in association with the stored images. The stored images are classified on the basis of the extracted keywords to generate a plurality of groups. For each of the generated groups, a centroid vector of wavelet feature-based feature vectors of respective images corresponding to the keywords is calculated and a spatial distance between the calculated centroid vector and each of the wavelet feature-based feature vectors is calculated. For each of the groups, the image for which the calculated spatial distance is the shortest and the radiographic interpretation information associated with the image is stored as a representative image of that group.

6 Claims, 8 Drawing Sheets

(51) Int. Cl.
  *A61B 6/00* (2006.01)
  *G06K 9/46* (2006.01)
  *G06F 19/00* (2011.01)

(56) References Cited

U.S. PATENT DOCUMENTS

| | | | |
|---|---|---|---|
| 8,189,883 B2* | 5/2012 | Oosawa et al. | 382/128 |
| 8,380,013 B2* | 2/2013 | Hisanaga et al. | 382/305 |
| 2003/0179213 A1* | 9/2003 | Liu | 345/619 |
| 2004/0267740 A1* | 12/2004 | Liu et al. | 707/3 |
| 2005/0244082 A1* | 11/2005 | Yamatake | 382/305 |
| 2007/0201754 A1* | 8/2007 | Li | 382/240 |
| 2009/0097756 A1* | 4/2009 | Kato | 382/190 |
| 2011/0099032 A1* | 4/2011 | Miyasa et al. | 705/3 |
| 2012/0183191 A1* | 7/2012 | Nakamura | 382/128 |

FOREIGN PATENT DOCUMENTS

| | | |
|---|---|---|
| JP | 2004254742 A | 9/2004 |
| JP | 2007279942 A | 10/2007 |
| JP | 2009297365 A | 12/2009 |
| JP | 2010079568 A | 4/2010 |
| JP | 2011040050 A | 2/2011 |

OTHER PUBLICATIONS

Int'l Bureau of WIPO, PCT/JP2012/074077, English Translation of Int'l Preliminary Examination Report and Written Opinion dated Jun. 26, 2014 (7 pg).

Int'l Bureau of WIPO, PCT/JP2012/074077, Int'l Preliminary Examination Report and Written Opinion dated Jun. 26, 2014 (6 pg).

* cited by examiner 1 1:0.64 2:0.49 3:0.32 4:1.68 5:7.97 6:5.90 7:1.09 8:0.37 9:0.59 10:0.21
11:0.40 12:1.43 13:4.32 14:3.55 15:0.90 16:0.61 17:0.43 18:0.13 19:0.80
20:1.62 21:2.18 22:1.67 23:0.59 24:0.65
2 1:0.46 2:0.53 3:0.71 4:2.90 5:10.51 6:8.30 7:1.99 8:0.52 9:0.71 10:0.42
11:0.47 12:2.37 13:6.74 14:4.89 15:1.50 16:0.55 17:0.64 18:0.27 19:0.15
20:1.33 31:3.93 22:2.37 23:1.12 24:0.44
3 1:0.20 2:0.41 3:1.15 4:3.43 5:13.40 6:9.19 7:1.56 8:0.29 9:0.58 10:0.58
11:0.96 12:2.80 13:9.97 14:7.08 15:2.04 16:0.63 17:0.65 18:0.41 19:0.80
20:2.77 21:8.63 22:5.33 23:2.09 24:0.86

FIG. 6

| SITE | LEFT LUNG FIELD, UPPER LOBE |
|---|---|
| SYMPTOM | NODULAR SHADOW |
| DISEASE NAME | SQUAMOUS CELL CARCINOMA SUSPECTED |
| ACTION | WORKUP BY HR-CT |

FIG. 7

TECHNIQUES FOR GENERATING A REPRESENTATIVE IMAGE AND RADIOGRAPHIC INTERPRETATION INFORMATION FOR A CASE

This application is a national stage of International Application No. PCT/JP2012/074077, entitled "METHOD, APPARATUS, AND COMPUTER PROGRAM FOR GENERATING REPRESENTATIVE IMAGE AND RADIOGRAPHIC INTERPRETATION INFORMATION FOR EACH CASE," filed Sep. 20, 2012, which claims priority to Japanese Patent Application No. 2011-272175, filed Dec. 13, 2011. The disclosure of International Application No. PCT/JP2012/074077 is hereby incorporated herein by reference in its entirety for all purposes.

BACKGROUND

The disclosure relates to image generation and, more specifically, to generating representative image and radiographic interpretation information on the basis of a plurality of stored images for a case.

In medical practice, it is important to recognize the internal states of a patient on the basis of images acquired by radiography. An X-ray image of a patient can be compared with X-ray images taken in the past to identify the causes of symptoms of the patient. This enables selection of appropriate medical treatment, leading to early improvement of the symptoms of the patient.

In the case of identifying a patient's symptoms from an X-ray image of the patient, images taken and stored in the past may be searched for a similar image, so as to confirm which case looks similar to the symptoms of the patient. For example, Japanese Unexamined Patent Publication No. 2007-279942 discloses a similar case search apparatus which searches for a similar case image and similar case data on the basis of feature values obtained from a diagnosis object image.

BRIEF SUMMARY

A technique for generating a representative image representing a case and radiographic interpretation information for each case from medical images based on past cases includes calculating wavelet features of a plurality of images that have been taken and stored in the past. A keyword included in radiographic interpretation information is extracted for each of the stored images. The calculated wavelet features and the extracted keywords are stored in association with the respective stored images. The stored images are classified on the basis of the extracted keywords to generate a plurality of groups. For each of the generated groups, a centroid vector of wavelet feature-based feature vectors of respective images corresponding to the keywords included in that group is calculated. For each of the groups, a spatial distance between the calculated centroid vector and each of the wavelet feature-based feature vectors of the respective images corresponding to the keywords included in that group is calculated. For each of the groups, the image for which the calculated spatial distance is the shortest and the radiographic interpretation information associated with the image is stored as a representative image of that group.

The above summary contains simplifications, generalizations and omissions of detail and is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed written description.

The above as well as additional objectives, features, and advantages of the present invention will become apparent in the following detailed written description.

BRIEF DESCRIPTION OF THE DRAWINGS

The description of the illustrative embodiments is to be read in conjunction with the accompanying drawings, wherein:

FIG. 6 shows, by way of example, the data structure of visual words stored in a visual word storage unit in a case image generating apparatus according to an embodiment of the present disclosure;

FIG. 7 shows, by way of example, keyword extraction by a case image generating apparatus according to an embodiment of the present disclosure;

DETAILED DESCRIPTION

Figure 1:
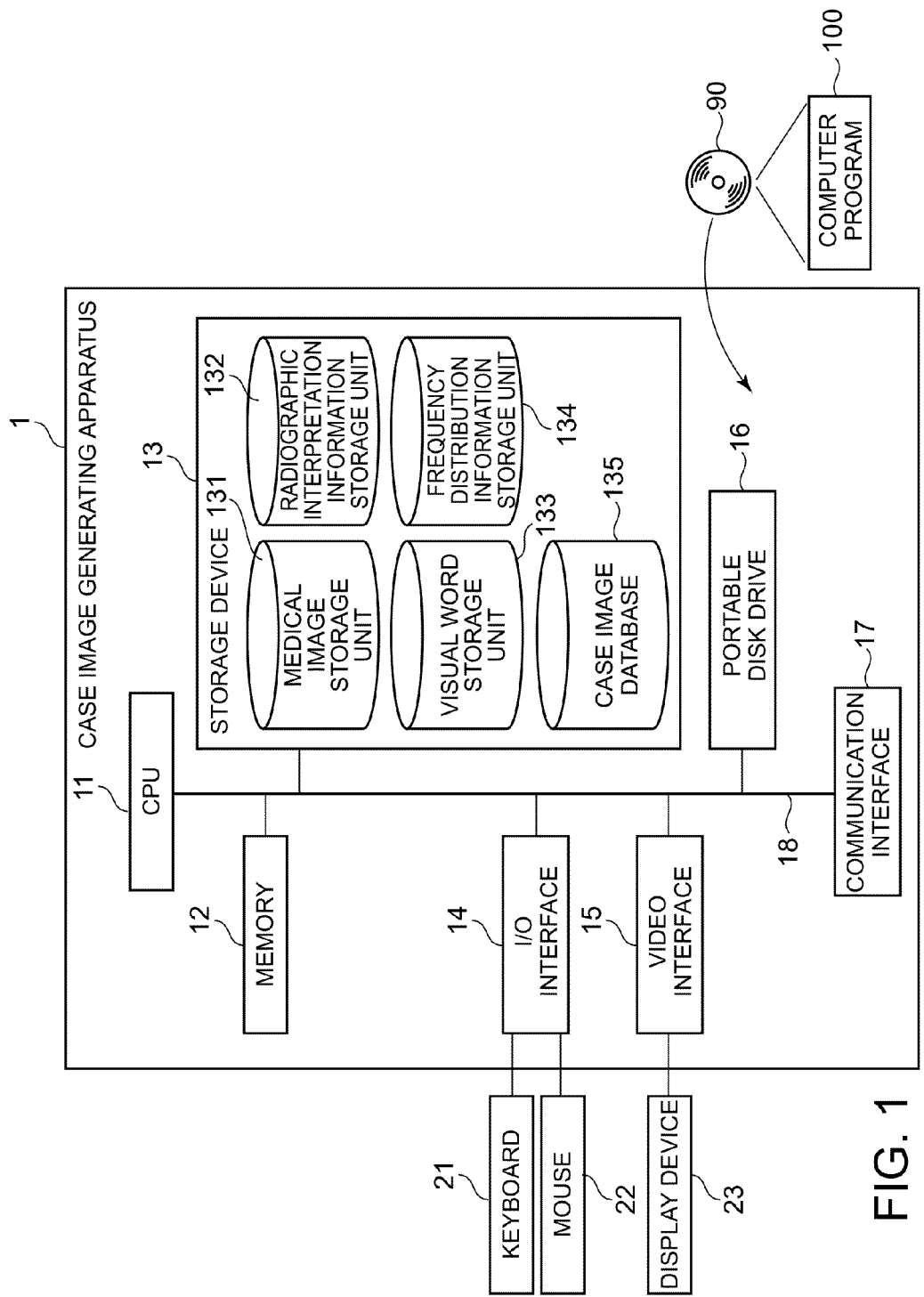
FIG. 1 is a block diagram schematically showing the configuration of a case image generating apparatus according to an embodiment of the present disclosure.

The illustrative embodiments provide a method, an apparatus, and a computer program product configured to generate a representative image and radiographic interpretation information for each case on the basis of stored past images.

In the following detailed description of exemplary embodiments of the invention, specific exemplary embodiments in which the invention may be practiced are described in sufficient detail to enable those skilled in the art to practice the invention, and it is to be understood that other embodiments may be utilized and that logical, architectural, programmatic, mechanical, electrical and other changes may be made without departing from the spirit or scope of the present invention. The following detailed description is, therefore, not to be taken in a limiting sense, and the scope of the present invention is defined by the appended claims and equivalents thereof.

It should be understood that the use of specific component, device, and/or parameter names are for example only and not meant to imply any limitations on the invention. The invention may thus be implemented with different nomenclature/terminology utilized to describe the components/devices/parameters herein, without limitation. Each term utilized herein is to be given its broadest interpretation given the context in which that term is utilized. As may be used herein, the term 'coupled' may encompass a direct connection between components or elements or an indirect connection between components or elements utilizing one or more intervening components or elements.

While the similar case search apparatus disclosed in Japanese Unexamined Patent Publication No. 2007-279942 is capable of searching for an image similar to the image of the patient, usually a plurality of similar images are found. While the similar case search apparatus is able to display the images in descending order of similarity, a large number of images different in symptoms, though similar in image feature, are found, and therefore the similar case search apparatus has a problem that it might be difficult to identify the symptoms in some cases.

In addition, although the apparatus is able to search stored images that have been classified according to cases, it is not possible to determine which one is a representative image, and therefore none of the valuable past images can be used as a guideline image for a case.

The disclosed embodiments have been provided in view of the above background and are configured to generate a representative image and radiographic interpretation information for each case on the basis of stored past images.

A method according to the present disclosure is capable of being executed in an apparatus to generate a representative image representing a case and radiographic interpretation information for each case from medical images based on past cases. In at least one embodiment, the method includes: calculating wavelet features of a plurality of images that have been taken and stored in the past; extracting a keyword included in radiographic interpretation information for each stored image; storing the calculated wavelet features and the extracted keywords in association with the respective stored images; classifying the stored images on the basis of the extracted keywords to generate a plurality of groups; calculating, for each of the generated groups, a centroid vector of wavelet feature-based feature vectors of respective images corresponding to the keywords included in that group; calculating, for each of the groups, a spatial distance between the calculated centroid vector and each of the wavelet feature-based feature vectors of the respective images corresponding to the keywords included in that group; and storing, for each of the groups, the image the calculated spatial distance of which is the shortest and the radiographic interpretation information associated with the image, as a representative image of that group.

The method may calculate a two-dimensional Gabor wavelet feature as the wavelet feature.

The method may also include calculating frequency distribution vectors for all images, by calculating M said wavelet features (M is a natural number of 2 or greater) for each image and binarizing the respective wavelet features for conversion into an M-dimensional bit string. The spatial distance may then be calculated as an angle between the centroid vector and each of the calculated frequency distribution vectors.

An apparatus configured according to the present disclosure may be configured to generate a representative image representing a case and radiographic interpretation information for each case from medical images based on past cases. The apparatus may include: a wavelet feature calculation unit for calculating wavelet features of a plurality of images that have been taken and stored in the past; a keyword extraction unit for extracting a keyword included in radiographic interpretation information for each stored image; an information storage unit for storing the calculated wavelet features and the extracted keywords in association with the respective stored images; a group generation unit for classifying the stored images on the basis of the extracted keywords to generate a plurality of groups; a centroid vector calculation unit for calculating, for each of the generated groups, a centroid vector of wavelet feature-based feature vectors of respective images corresponding to the keywords included in that group; a spatial distance calculation unit for calculating, for each of the groups, a spatial distance between the calculated centroid vector and each of the wavelet feature-based feature vectors of the respective images corresponding to the keywords included in that group; and a representative image storage unit for storing, for each of the groups, the image the calculated spatial distance of which is the shortest and the radiographic interpretation information associated with the image, as a representative image of that group.

The wavelet feature calculation unit may calculate a two-dimensional Gabor wavelet feature as the wavelet feature.

The apparatus may further include a frequency distribution vector calculation unit for calculating frequency distribution vectors for all images, by calculating M said wavelet features (M is a natural number of 2 or greater) for each image and binarizing the respective wavelet features for conversion into an M-dimensional bit string. The spatial distance calculation unit may then calculate the spatial distance as an angle between the centroid vector and each of the calculated frequency distribution vectors.

A computer program executable by an apparatus may be configured to generate a representative image representing a case and radiographic interpretation information for each case, from medical images based on past cases. The program may cause the apparatus to function as: a wavelet feature calculation unit for calculating wavelet features of a plurality of images that have been taken and stored in the past; a keyword extraction unit for extracting a keyword included in radiographic interpretation information for each stored image; an information storage unit for storing the calculated wavelet features and the extracted keywords in association with the respective stored images; a group generation unit for classifying the stored images on the basis of the extracted keywords to generate a plurality of groups; a centroid vector calculation unit for calculating, for each of the generated groups, a centroid vector of wavelet feature-based feature vectors of respective images corresponding to the keywords included in that group; a spatial distance calculation unit for calculating, for each of the groups, a spatial distance between the calculated centroid vector and each of the wavelet feature-based feature vectors of the respective images corresponding to the keywords included in that group; and a representative image storage unit for storing, for each of the groups, the image the calculated spatial distance of which is the shortest and the radiographic interpretation information associated with the image, as a representative image of that group.

The computer program may be configured to cause the wavelet feature calculation unit to function as unit for calculating a two-dimensional Gabor wavelet feature as the wavelet feature.

The program may be further configured to cause the apparatus to function as frequency distribution vector calculation unit for calculating frequency distribution vectors for all images, by calculating M said wavelet features (M is a natural number of 2 or greater) for each image and binarizing the respective wavelet features for conversion into an M-dimensional bit string. The program may cause the spatial distance calculation unit to function as unit for calculating the spatial distance as an angle between the centroid vector and each of the calculated frequency distribution vectors.

According to the present disclosure, wavelet features indicating the features of stored medical images are used to calculate feature vectors for the respective images, and from these feature vectors, a centroid vector is calculated as a feature vector for each case. Among the stored medical images, an image having the feature vector with the shortest spatial distance from the centroid vector is stored as a representative image. Therefore, the image indicating a typical case can be used as a guideline of the case, allowing a diagnosis to be made for a patient at a certain level of quality, without being affected by experience or expertise of each doctor.

A case image generating apparatus for generating a representative image and radiographic interpretation information for each case out of medical images based on past cases according to an embodiment is specifically described below with reference to the drawings. The following embodiments do not restrict the claimed invention, and all the combinations of the features described in the embodiment are not necessarily indispensable.

Further, the present invention can be carried out in many different modes, and should not be understood only from the description given. Through the whole description of the embodiment, the same elements are denoted by the same reference numerals.

While an apparatus comprising a computer system having a computer program introduced therein is described, it should be apparent to those skilled in the art that part of the present invention may be implemented as a computer-executable computer program. Therefore, the present invention can take the form of an embodiment as hardware which is a case image generating apparatus that generates a representative image and radiographic interpretation information for each case out of medical images based on past images or an embodiment as a combination of software and hardware. The computer program may be recorded on an arbitrary computer-readable recording medium, such as a hard disk, a DVD, a CD, an optical storage device, or a magnetic storage device.

According to one embodiment, wavelet features indicating the features of stored medical images are used to calculate feature vectors for the respective images, and from these feature vectors, a centroid vector is calculated as a feature vector for each case. Among the stored medical images, an image having the feature vector with the shortest spatial distance from the centroid vector is stored as a representative image. Therefore, the image indicating a typical case can be used as a guideline of the case, allowing a diagnosis to be made for a patient at a certain level of quality, without being affected by experience or expertise of each doctor.

FIG. 1 is a block diagram schematically showing the configuration of a case image generating apparatus (e.g., computer system) according to an embodiment of the present disclosure. The case image generating apparatus 1 according to the embodiment at least includes: a central processing unit (CPU) or processor 11, a memory 12, a storage device 13, an I/O interface 14, a video interface 15, a portable disk drive 16, a communication interface 17, and an internal bus 18 for connecting the above-described hardware components.

The CPU 11 is connected via the internal bus 18 to the hardware components of the case image generating apparatus 1 as described above. The CPU 11 controls the operations of those hardware components, and also executes various software functions in accordance with a computer program 100 stored in the storage device 13. The memory 12 is made up of a volatile memory such as an SRAM or an SDRAM, in which a load module is deployed at the time of execution of the computer program 100. Temporary data generated during the execution of the computer program 100 is also stored in the memory 12.

The storage device 13 includes a built-in fixed storage (hard disk), a ROM, and others. The computer program 100 stored in the storage device 13 is one that has been downloaded by the portable disk drive 16 from a portable recording medium 90 such as a DVD or a CD-ROM that records information such as data and programs. At run-time, the computer program 100 is deployed from the storage device 13 to the memory 12 for execution. The computer program 100 may of course be downloaded from an external computer connected via the communication interface 17.

The storage device 13 includes a medical image storage unit 131, a radiographic interpretation information storage unit 132, a visual word storage unit 133, a frequency distribution information storage unit 134, and a case image database 135. The medical image storage unit 131 stores image data of X-ray images taken in the past. The unit 131 stores the image data in association with identification information for identifying radiographic interpretation information.

The radiographic interpretation information storage unit 132 stores results of diagnoses that doctors have made by interpreting medical images taken in the past. For example, a doctor's diagnosis such as "nodular shadow found in left lung field, upper lobe; squamous cell carcinoma suspected; workup by HR-CT instructed" is stored in the form of text data in association with identification information.

The visual word storage unit 133 stores, as visual words, Gabor wavelet features which will be described later. The frequency distribution information storage unit 134 stores, as feature vectors, frequency distribution vectors of values obtained by binarizing calculated wavelet features and converting them into M-dimensional bit strings.

The case image database 135 stores, for each case, a representative image as the most typical image for that case and radiographic interpretation information corresponding to the representative image, in the form of database. The case image database 135 functions as guidelines for cases, from which a typical image for each case can be extracted. This allows a diagnosis to be made for a patient at a certain level of quality, without being affected by experience or expertise of each doctor.

The communication interface 17 is connected to the internal bus 18, and to an external network such as the Internet, a LAN, or a WAN, so that it is able to transmit data to and receive data from an external computer.

The I/O interface 14 is connected to input devices such as a keyboard 21 and a mouse 22, and accepts input of data. The video interface 15 is connected to a display device 23 such as a CRT display or a liquid crystal display, and displays a representative image and radiographic interpretation information corresponding to the representative image on the display device 23.

Figure 2:
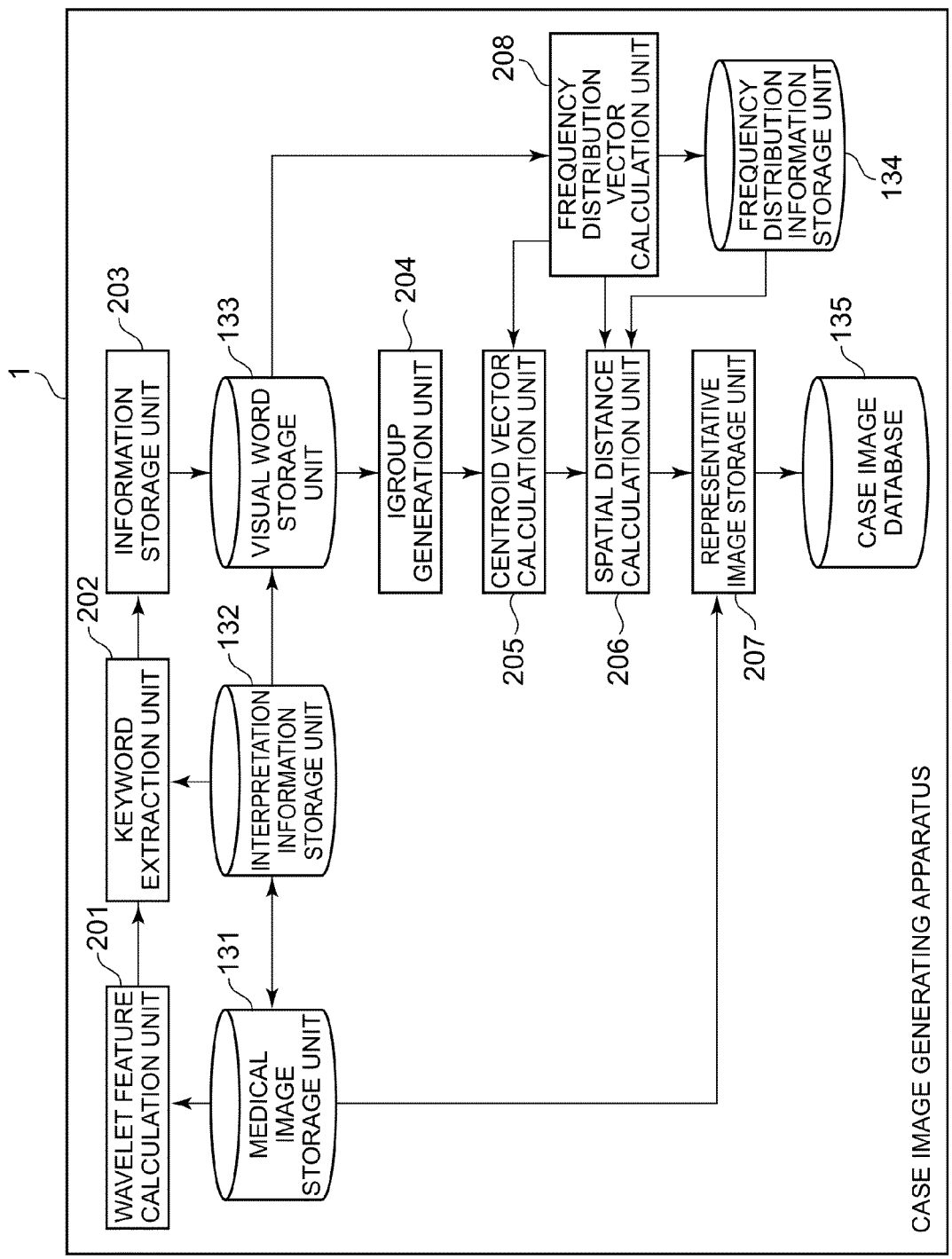
FIG. 2 is a functional block diagram of a case image generating apparatus according an embodiment of the present disclosure.

FIG. 2 is a functional block diagram of the case image generating apparatus 1 according to one embodiment. Referring to FIG. 2, a wavelet feature calculation unit 201 in the case image generating apparatus 1 calculates wavelet features of a plurality of images taken and stored in the past. In one embodiment, Gabor wavelet features are calculated as the wavelet features.

Figure 3:
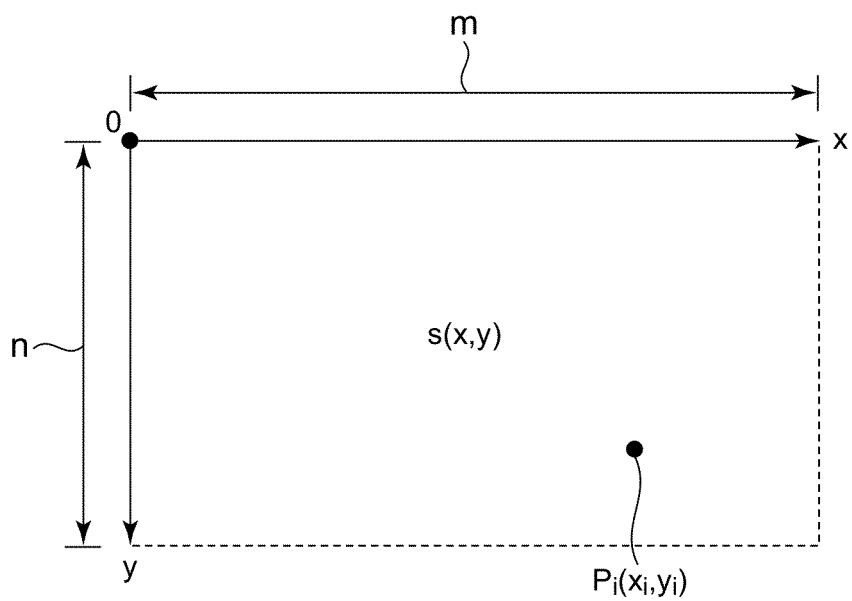
FIG. 3 illustrates coordinate setting within an image used in a case image generating apparatus according to an embodiment of the present disclosure.

FIG. 3 illustrates coordinate setting within an image used in the case image generating apparatus 1 according to one embodiment. As shown in FIG. 3, an image with an origin at an upper left corner thereof and having m pixels in an x direction and n pixels in a y direction is defined as s(x, y). The coordinates of an i-th pixel $P_i$ (i is a natural number) are represented as $P_i(x_i, y_i)$.

First, the coordinates $P_i(x_i, y_i)$ are affine-transformed to coordinates $(X_i, Y_i)$ in accordance with the following expression (1).

$$[X_i, Y_i, 1] = [x_i, y_i, 1]A \quad (1)$$

In the above expression (1), the matrix A is a 3×3 affine transformation matrix. The affine transformation to shift the entire image by tx in the x direction and by ty in the y direction can be expressed by the following expression (2), and the affine transformation to rotate the entire image by an angle θ can be expressed by the following expression (3).

$$[X_i, Y_i, 1] = [x_i, y_i, 1] \begin{bmatrix} 1 & 0 & 0 \\ 0 & 1 & 0 \\ tx & ty & 1 \end{bmatrix} \quad (2)$$

$$[X_i, Y_i, 1] = [x_i, y_i, 1] \begin{bmatrix} \cos\theta & \sin\theta & 0 \\ -\sin\theta & \cos\theta & 0 \\ 0 & 0 & 1 \end{bmatrix} \quad (3)$$

A two-dimensional Gabor wavelet function is defined, with respect to the coordinate values (x with dot, y with dot) after the affine transformation for rotation, as in the following expression (4).

$$\psi_r(x, y) = g_\sigma(\dot{x}, \dot{y})\left[e^{iu_0\dot{x}} - e^{-(u_0\sigma)^2}\right] \quad (4)$$

$$\begin{bmatrix} \dot{x} \\ \dot{y} \end{bmatrix} = \begin{bmatrix} \cos\theta_r & \sin\theta_r \\ -\sin\theta_r & \cos\theta_r \end{bmatrix} \begin{bmatrix} x \\ y \end{bmatrix}$$

Figure 4A:
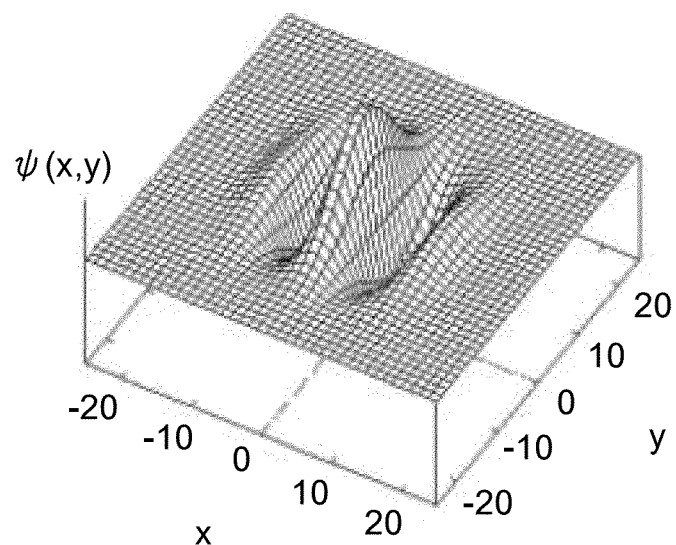
FIGS. 4A and 4B show, by way of example, a two-dimensional Gabor wavelet function.
Figure 4B:
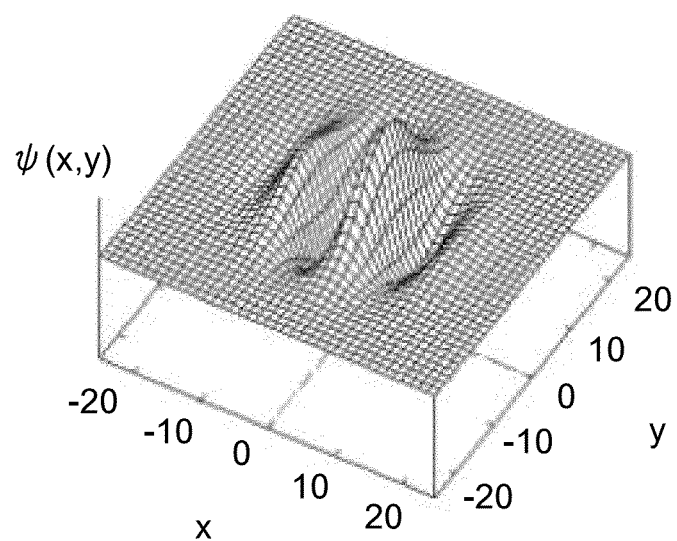

The two-dimensional Gabor wavelet function is composed of a real part and an imaginary part. FIGS. 4A and 4B show an example of a two-dimensional Gabor wavelet function. Specifically, FIGS. 4A and 4B show examples of the real part and imaginary part, respectively, of the two-dimensional Gabor wavelet function. As seen from FIGS. 4A and 4B, the real part of the two-dimensional Gabor wavelet function has a hat-like wavy form with its maximum value located near (x, y)=(0, 0). In the above expression (4), $u_0$ represents the frequency of that waveform, and σ represents the width of that hat shape. Further, r represents the direction, which will be described later.

The window function $g_\sigma$ in the above expression (4) is a two-dimensional Gaussian function, which can be expressed by the following expression (5).

$$g_\sigma(\dot{x}, \dot{y}) = \frac{1}{4\pi\sigma}e^{\frac{-1}{4\sigma^2}(\dot{x}^2+\dot{y}^2)} \quad (5)$$

Using the two-dimensional Gabor wavelet function, the Gabor wavelet features for an acquired image s(x, y) can be calculated by the following expression (6). The lattice point at which the absolute value of the Gabor wavelet feature has a maximum value and the Gabor wavelet features in the vicinity of that lattice point are invariant even when the image is subjected to affine transformation such as scaling, rotation, etc., so that they are suitably used as the feature values of an image.

$$G_{j,r}(x_0, y_0) = a^{-j} \int\int s(x, y)\psi_r\left(\frac{x-x_0}{a^j}, \frac{y-y_0}{a^j}\right)dxdy \quad (6)$$

In the above expression (6), $a^j$ and $a^{-j}$ are parameters indicating the degrees of dilation (scaling), and $x_0$ and $y_0$ represent shift. Further, r represents the direction. In the present embodiment, the Gabor wavelet features in eight directions are calculated.

Figure 5:
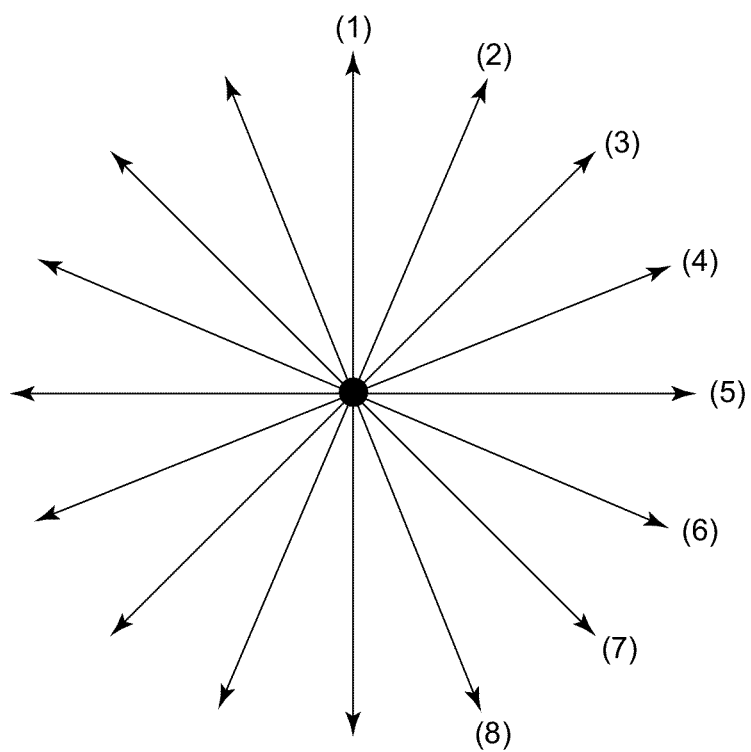
FIG. 5 is a schematic diagram showing the directions of the two-dimensional Gabor wavelet function used in a case image generating apparatus according to an embodiment of the present disclosure.

FIG. 5 is a schematic diagram showing the directions of the two-dimensional Gabor wavelet function used in the case image generating apparatus 1 according to one embodiment. As shown in FIG. 5, in the present embodiment, the Gabor wavelet features are calculated in directions (1) to (8), i.e., in eight directions spaced every 22.5 degrees from a prescribed direction.

The calculation of the Gabor wavelet features makes it possible to calculate the wavelet feature values that accommodate or absorb variations in shape of the human organs, for example, so that a more appropriate representative image can be selected from among the images related to the same case.

For example, in the case where the above expression (6) is used to calculate the Gabor wavelet features for each coordinate point (x, y) (lattice point within an image), eight directions (r=1 to 8) and five scales (j=1 to 5) are selected to calculate 40 Gabor wavelet features for one coordinate point. Here, the scales 1 to 5 indicate the levels of enlargement/reduction. For example, a greater value indicates a greater degree of enlargement. From the Gabor wavelet features calculated, those having the absolute values of not less than a predetermined threshold value are extracted, and the Gabor wavelet feature having a maximum value among them is selected.

The fact that the absolute value of the Gabor wavelet feature takes a maximum value unit that the absolute value of the integral in the above expression (6) is maximum. The feature value remains unchanged even when the average brightness of the image is changed, the scale of the image is changed, or the image is rotated.

In the present embodiment, the Gabor wavelet features in eight directions in the scale where a maximum value is obtained, as well as the Gabor wavelet features in the eight directions in each of the neighboring scales, namely 24 (3 scales×8 directions) Gabor wavelet features in total, are stored as a set of visual words in the visual word storage unit 133.

FIG. 6 shows, by way of example, the data structure of visual words stored in the visual word storage unit 133 in the storage device 13 in the case image generating apparatus 1 according to one embodiment. As shown in FIG. 6, 24 Gabor wavelet features which have been calculated are listed and stored corresponding to each identification number 1, 2, 3, .... More specifically, "1" at the beginning is the identification number, which is followed by a blank space, and the numerical values following "1:" to "24:" are the 24 Gabor wavelet features calculated. FIG. 6 shows the visual words in the case where there are three maximum values within one image. Thus, in FIG. 6, the visual words are stored corresponding to three identification numbers "1", "2", and "3". When there is one maximum value, there is naturally only one identification number "1".

Returning to FIG. 2, a keyword extraction unit 202 extracts keywords that are included in the radiographic interpretation information stored in the radiographic interpretation information storage unit 132 in the storage device 13 corresponding to the past images stored in the medical image storage unit 131 in the storage device 13. For example, in the case where radiographic interpretation information reading: "nodular shadow found in left lung field, upper lobe; squamous cell carcinoma suspected; workup by HR-CT instructed" is stored in the radiographic interpretation information storage unit 132 in the storage device 13, syntax analysis is carried out using morphological analysis or the like to extract keywords, which are classified as "site", "symptom", "disease name", "action", etc.

FIG. 7 shows, by way of example, keyword extraction by the case image generating apparatus 1 according to an embodiment. In the example shown in FIG. 7, through the syntactic analysis of "nodular shadow found in left lung field, upper lobe; squamous cell carcinoma suspected; workup by HR-CT instructed", the following keywords have been extracted: "left lung field, upper lobe" as "site", "nodular shadow" as "symptom", "squamous cell carcinoma suspected" as "disease name", and "workup by HR-CT" as "action".

Returning to FIG. 2, an information storage unit 203 stores the wavelet features calculated in the above-described manner and the extracted keywords, in the visual word storage unit 133 in the storage device 13. The unit 203 stores the wavelet features and the keywords in association with the past images stored in the medical image storage unit 131 in the storage device 13.

A group generation unit 204 classifies the stored images on the basis of the extracted keywords to generate a plurality of groups. While the categories for classification are not particularly restricted, a plurality of groups are preferably generated by classifying the images under the items used in the syntax analysis, i.e. "site", "symptom", "disease name" etc., and/or one or more combinations thereof. One image may of course be classified into more than one group.

A centroid vector calculation unit 205 calculates, for each group, a centroid vector of wavelet features of the images corresponding to the keywords included in that group. More specifically, for each of the images included in the group, M wavelet features (M is a natural number of 2 or greater), for example 24 wavelet features, are calculated for each pixel, and the calculated wavelet features are binarized and converted to an M-dimensional bit string (M=24).

A frequency distribution vector calculation unit 208 generates a histogram indicating the frequency distribution of the values of the 24-dimensional bit strings obtained through conversion. Such a histogram is generated for all the images included in the group.

Figure 8:
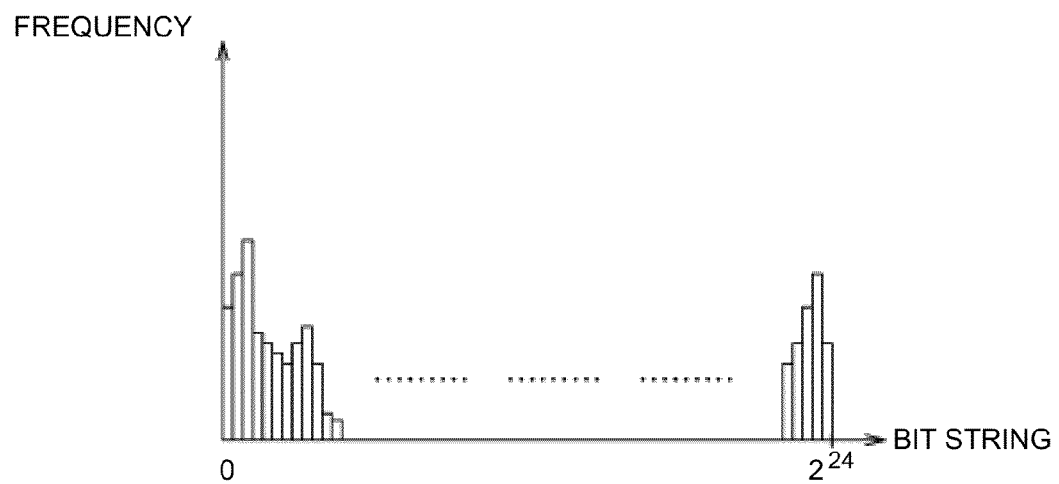
FIG. 8 shows, by way of example, a histogram according to an embodiment of the present disclosure.

FIG. 8 shows an example of a histogram according to one embodiment. In this example, $2^{24}$ values are taken along the horizontal axis, and frequency distribution is obtained for the respective values. Then, the frequency distribution for each image is stored as a frequency distribution vector, in the frequency distribution information storage unit 134 in the storage device 13.

The centroid vector calculation unit 205 uses the wavelet features and the calculated frequency distribution vectors of the images included in each of the groups to calculate a centroid vector of the frequency distribution vectors for each group, in accordance with the following expression (7). More specifically, the centroid vector $V_T$ of the frequency distribution vectors $V_i$ (i is the number of images included in the group) is calculated by dividing the total sum of the frequency distribution vectors $V_i$ by the total sum of the norms (lengths) of the frequency distribution vectors $V_i$.

$$V_T = \frac{\sum_i V_i}{\sum_i \|V_i\|} \tag{7}$$

Returning to FIG. 2, a spatial distance calculation unit 206 calculates a spatial distance between the calculated centroid vector and the wavelet feature-based feature vector (frequency distribution vector) of each of the images corresponding to the keywords included in the group. The spatial distance calculation unit 206 calculates the spatial distance as an angle between the centroid vector and the feature vector (frequency distribution vector). More specifically, when the frequency distribution vector of an image included in the group is represented as $V_i$ and the centroid vector is represented as $V_T$, then the spatial distance is calculated as the cosine of the angle $\phi$ between the two vectors, i.e. $\cos\phi$, in accordance with the following expression (8).

$$\cos\phi = \frac{\langle V_i, V_T \rangle}{\|V_i\| \cdot \|V_T\|} \tag{8}$$

In the above expression (8), $\langle V_i, V_T \rangle$ indicates the inner product of the vectors $V_i$ and $V_T$, and the denominator indicates the product between the norm (length) of the vector $V_i$ and the norm of the vector $V_T$.

Returning to FIG. 2, a representative image storage unit 207 stores the image the calculated spatial distance of which is the shortest and radiographic interpretation information associated with that image, as a representative image of the group, in the case image database 135. The image having a shorter spatial distance is closer to the centroid vector of the images included in the group, and therefore it is suitably used as a representative image for a case.

Figure 9:
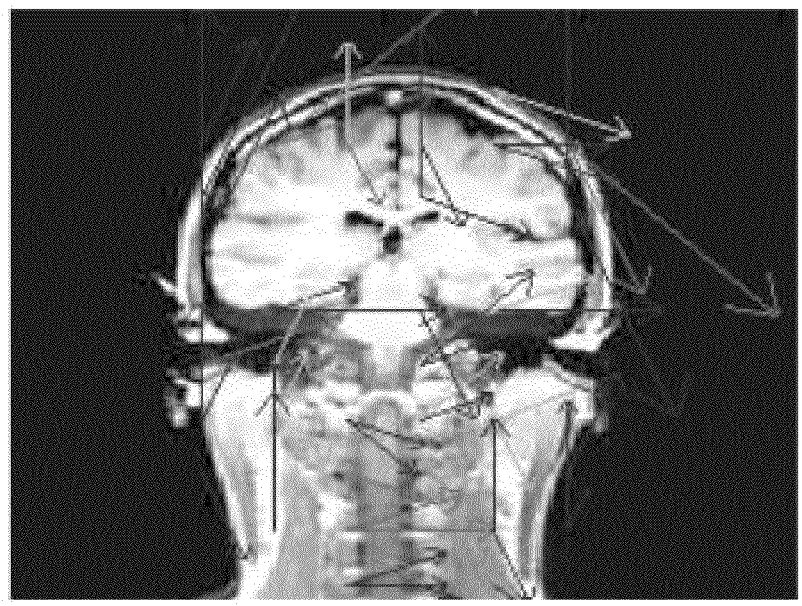
FIG. 9 shows an example of a representative image display screen used in a case image generating apparatus according to an embodiment of the present disclosure.

It is noted that when a representative image is displayed on the display device 23, feature vectors may be overlaid on the displayed image. FIG. 9 shows an example of a representative image display screen used in the case image generating apparatus 1 according to one embodiment.

As shown in FIG. 9, a past image that has been determined to be closest to the centroid vector is displayed as the representative image and, of the wavelet features, those greater than a predetermined value are displayed overlaid on the image as the feature vectors. The length of each arrow indicates the magnitude of the feature value. The direction of each arrow indicates the one of the eight directions in which the feature value is greatest. The scales may also be distinguished by colors, line types, and so on.

Figure 10:
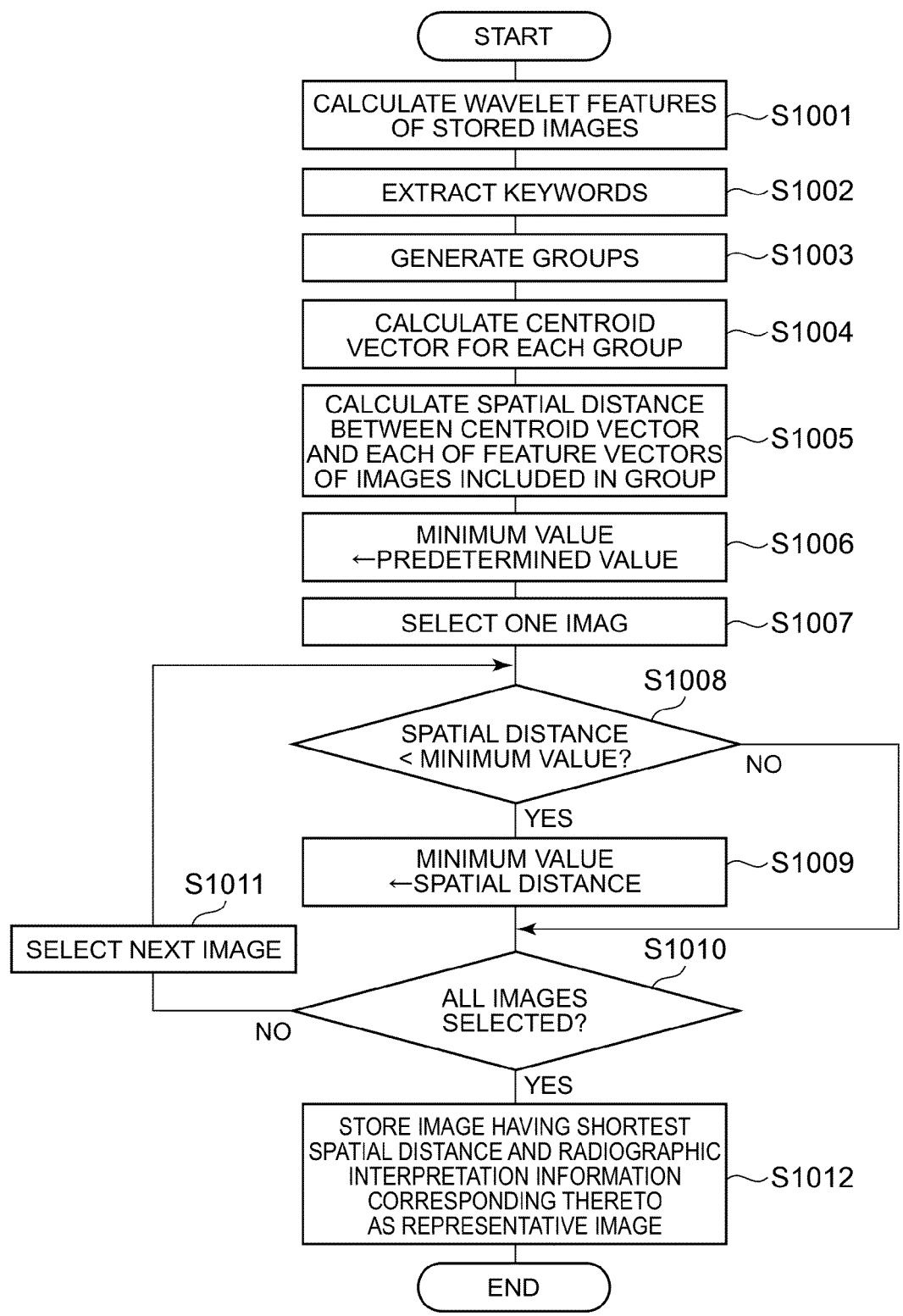
FIG. 10 is a flowchart illustrating a processing procedure of a CPU in a case image generating apparatus according to an embodiment of the present disclosure.

FIG. 10 is a flowchart illustrating the processing procedure of the CPU 11 in the case image generating apparatus 1 according to one embodiment. Referring to FIG. 10, the CPU 11 in the case image generating apparatus 1 calculates wavelet features of a plurality of images that have been taken and stored in the past (S1001). In the present embodiment, Gabor wavelet features are calculated as the wavelet features.

The CPU 11 extracts keywords included in the radiographic interpretation information for the respective stored past images (S1002), and stores the extracted keywords and the wavelet features calculated in the above-described manner, in association with the stored past images.

The CPU 11 generates a plurality of groups by classifying the stored images on the basis of the extracted keywords (S1003). While the categories for classification are not particularly restricted, a plurality of groups are preferably generated by classifying the images under the items used in the syntax analysis, i.e. "site", "symptom", "disease name", etc., and/or one or more combinations thereof. One image may of course be classified into more than one group.

The CPU 11 calculates, for each group, a centroid vector as a feature vector, on the basis of the wavelet features of the images included in the group (S1004). The CPU 11 calculates a spatial distance between the calculated centroid vector and the wavelet feature-based feature vector (frequency distribution vector) of each of the images corresponding to the keywords included in the group (S1005).

The CPU 11 sets a predetermined value as a minimum value (S1006), and selects one of the images included in the group (S1007). The CPU 11 determines whether the spatial distance calculated for the selected image is smaller than the minimum value (S1008).

If the CPU 11 determines that it is smaller than the minimum value (YES in S1008), the CPU 11 stores the spatial distance as the minimum value (S1009). If the CPU 11 determines that the spatial distance calculated is not smaller than the minimum value (NO in S1008), the CPU 11 skips S1009. The CPU 11 determines whether all the images have been selected (S1010). If the CPU 11 determines that there is an image yet to be selected (NO in S1010), the CPU 11 selects a next image (S1011). The process then returns to S1008, and the above-described processing is repeated.

If the CPU 11 determines that all the images have been selected (YES in S1010), the CPU 11 stores the image corresponding to the spatial distance stored as the minimum value and the radiographic interpretation information corresponding thereto, as a representative image, in the case image database 135 (S1012).

As described above, according to the present embodiment, wavelet features indicating the features of stored medical images are used to calculate feature vectors for the respective images, and from these feature vectors, a centroid vector is calculated as a feature vector for each case. Among the stored medical images, an image having the feature vector with the shortest spatial distance from the centroid vector is stored as a representative image. Therefore, the image indicating a typical case can be used as a guideline of the case, allowing a diagnosis to be made for a patient at a certain level of quality, without being affected by experience or expertise of each doctor.

It is noted that the present invention is not restricted to the above-described embodiment; a variety of modifications and improvements are possible within the scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiberoptic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the invention has been described with reference to exemplary embodiments, it will be understood by those skilled in the art that various changes may be made and equivalents may be substituted for elements thereof without departing from the scope of the invention. In addition, many modifications may be made to adapt a particular system, device or component thereof to the teachings of the invention without departing from the essential scope thereof. Therefore, it is intended that the invention not be limited to the particular embodiments disclosed for carrying out this invention, but that the invention will include all embodiments falling within the scope of the appended claims. Moreover, the use of the terms first, second, etc. do not denote any order or importance, but rather the terms first, second, etc. are used to distinguish one element from another.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

What is claimed is:

1. An apparatus for generating a representative image representing a case and radiographic interpretation information for each case from medical images based on past cases, comprising:
    a wavelet feature calculation unit configured to calculate wavelet features of a plurality of images that have been taken and stored in the past;
    a keyword extraction unit configured to extract a keyword included in radiographic interpretation information for each of the stored images;
    an information storage unit configured to store the calculated wavelet features and the extracted keywords in association with the respective stored images;
    a group generation unit configured to classify the stored images on the basis of the extracted keywords to generate a plurality of groups;
    a centroid vector calculation unit configured to calculate, for each of the generated groups, a centroid vector of wavelet feature-based feature vectors of respective images corresponding to the keywords included in that group;
    a spatial distance calculation unit configured to calculate, for each of the groups, a spatial distance between the calculated centroid vector and each of the wavelet feature-based feature vectors of the respective images corresponding to the keywords included in that group; and
    a representative image storage unit configured to store, for each of the groups, the image for which the calculated spatial distance is the shortest and the radiographic interpretation information associated with the image as a representative image of that group.

2. The apparatus of claim 1, wherein the wavelet feature calculation unit calculates two-dimensional Gabor wavelet features.

3. The apparatus of claim 1, further comprising:
    a frequency distribution vector calculation unit for calculating frequency distribution vectors for all images by calculating M said wavelet features for each image and binarizing the respective wavelet features for conversion into an M-dimensional bit string, wherein the spatial distance calculation unit calculates the spatial distance as an angle between the centroid vector and each of the calculated frequency distribution vectors, and wherein M is a natural number of 2 or greater.

4. A computer program product, comprising:
    a computer-readable storage device; and
    program code embodied on the computer-readable storage device, wherein the program code, when executed by a processor, configures the processor to:
        calculate wavelet features of a plurality of images that have been taken and stored in the past;
        extract a keyword included in radiographic interpretation information for each of the stored images;

store the calculated wavelet features and the extracted keywords in association with the respective stored images;

classify the stored images on the basis of the extracted keywords to generate a plurality of groups;

calculate, for each of the generated groups, a centroid vector of wavelet feature-based feature vectors of respective images corresponding to the keywords included in that group;

calculate, for each of the groups, a spatial distance between the calculated centroid vector and each of the wavelet feature-based feature vectors of the respective images corresponding to the keywords included in that group; and store, for each of the groups, the image in which the calculated spatial distance is the shortest and the radiographic interpretation information associated with the image as a representative image of that group.

5. The computer program of claim 4, wherein the wavelet features are two-dimensional Gabor wavelet features.

6. The computer program of claim 4, wherein the program code, when executed by the processor, further configures the processor to:

calculate frequency distribution vectors for all images by calculating M said wavelet features for each image and binarizing the respective wavelet features for conversion into an M-dimensional bit string, wherein M is a natural number of 2 or greater; and calculate the spatial distance as an angle between the centroid vector and each of the calculated frequency distribution vectors.

* * * * *